United States Patent [19]

Derby et al.

[11] Patent Number: 4,460,572

[45] Date of Patent: Jul. 17, 1984

[54] SYNTHETIC RESINOUS POLYMER CONTAINING BIOLOGICALLY ACTIVE ORGANIC MATERIAL

[75] Inventors: Robert L. Derby, Lake Jackson, Tex.; Richard H. Hall; Howard L. Young, both of Midland, Mich.

[73] Assignee: The Dow Chemical Company, Midland, Mich.

[21] Appl. No.: 494,197

[22] Filed: May 13, 1983

Related U.S. Application Data

[63] Continuation-in-part of Ser. No. 392,119, Jun. 25, 1982, abandoned, which is a continuation-in-part of Ser. No. 259,864, May 4, 1981, abandoned, which is a continuation-in-part of Ser. No. 150,376, May 15, 1980, abandoned.

[51] Int. Cl.$^3$ .................. A61K 31/74; A01N 31/02; A01N 31/035
[52] U.S. Cl. .................................... 424/78; 424/80; 424/81; 424/83; 424/350; 424/351
[58] Field of Search .................. 424/78, 80, 81, 83, 424/350, 351

[56] References Cited

U.S. PATENT DOCUMENTS 3,876,761 4/1975 Shepherd .......................... 424/78

Primary Examiner—Sam Rosen
Attorney, Agent, or Firm—R. B. Ingraham

[57] ABSTRACT

A fumigant swellable fumigant insoluble cross-linked polymer is swollen with volatile fumigant such as 1,3-dichloropropene. Fumigant is released at a slower rate than if polymer is not employed.

18 Claims, 1 Drawing Figure

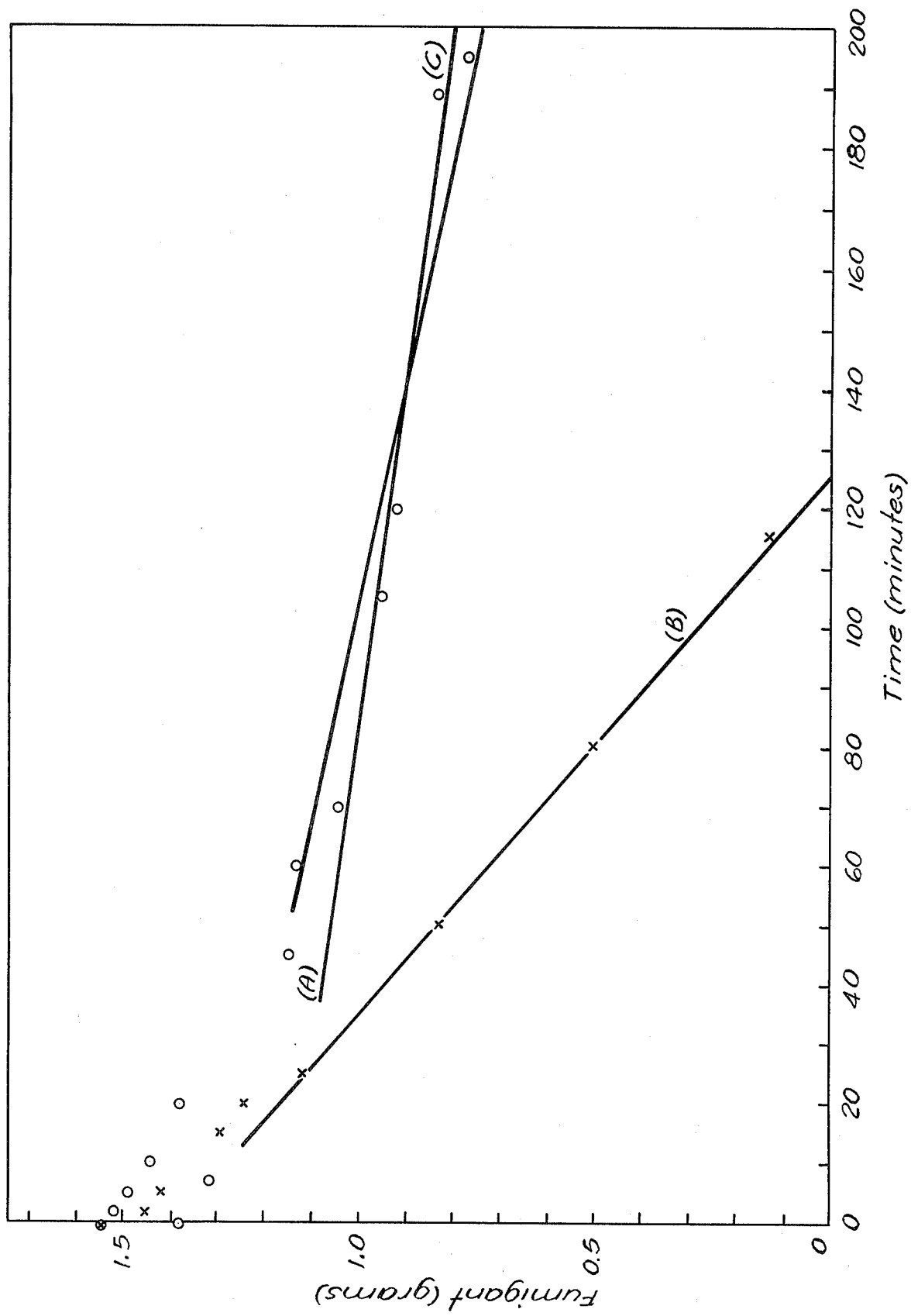

SYNTHETIC RESINOUS POLYMER CONTAINING BIOLOGICALLY ACTIVE ORGANIC MATERIAL

This application is a continuation-in-part of the copending application Ser. No. 392,119, filed June 25, 1982, which is a continuation-in-part of the copending application Ser. No. 259,864, filed May 4, 1981, which is a continuation-in-part of Ser. No. 150,376, filed May 15, 1980, all now abandoned.

A wide variety of organic chemical materials having biological activity are utilized for a wide variety of purposes. One purpose is as a pesticide which includes fungicides, insecticides, bacteriacides, nematocides and the like. Nitrogen stabilizing compounds are also employed with benefit. Many of these materials are provided in liquid form or in dust form, pellet form or all such three forms. Often certain problems are encountered as releasing material to the environment at a desired rate which is oftentimes different than the rate at which the commercially pure compound or composition would be released to the environment. Some such organic biologically active chemicals are of low hydrolytic stability and on exposure to water decompose into undesirable or ineffective by-products. Frequently, such biologically active materials are in a form which is not particularly convenient for handling such as any form of fine powders which can only be applied for example to a field under reasonably optimum conditions. Such fine powders generally require careful handling and from a standpoint of personal safety are relatively undesirable.

Various volatile organic chemical materials are employed as soil fumigants to reduce or eliminate crop damage from pests such as nematodes. Typical of such fumigants are 1,3-dichloropropene and 1,2-dibromoethane. Oftentimes, multiple applications of such materials must be made to the soil in the course of a growing season in order to obtain the desired pest control level. Generally, such materials are applied by a subsoil application as liquids at a depth in the general range of about twelve inches. Such an application usually in the course of a growing season must be repeated at least once and sometimes twice in order to achieve desired control.

It would be desirable if there were available an improved means of handling organic biologically active materials which would provide a degree of controlled release.

It would be desirable if there were available biologically active organic chemical compositions which would permit handling compositions in either liquid, particulate or solid form.

It would be desirable if there were a means of providing liquid soil fumigant in a form which would only require a single application during the growing season.

It would also be desirable if there were available means which would permit a choice of applying the material in a liquid-like form or in the form of granular solids.

It would also be desirable if there were available means to supply volatile liquid soil fumigant in improved form which would require less total fumigant for pest control during a growing season.

These benefits and other advantages in accordance with the present invention are achieved in a composition containing biologically active organic materials, the composition comprising a plurality of organic chemically swellable organic chemically insoluble crosslinked polymer particles, the polymer particles having a swelling index of from about 1.2 to 50; the particles having imbibed therein from about 1.2 to 50 times the unswollen volume of the particles of a biologically active organic chemical composition which is capable of diffusing out of said particles.

Also contemplated within the scope of the present invention is a method of dispensing a biologically active organic chemical composition by disposing said biologically active composition comprising a plurality of organic chemically swellable organic chemically insoluble crosslinked polymer particles, the polymer particles having a swelling index of from about 1.2 to 50; the polymer particles having imbibed therein from about 3 to 50 times the unswollen volume of the particles of a biologically active organic chemical composition which can diffuse from said particles.

Another desirable embodiment of the present invention is a fumigant composition, the fumigant composition comprising a plurality of fumigant swellable fumigant insoluble crosslinked polymer particles, the polymer particles having imbibed therein from about 1.2 to 50 times the unswollen volume of the particles of a volatile soil fumigant which boils at atmospheric pressure at a temperature of from about $-100°$ centigrade to $350°$ centigrade and advantageously from about $-100°$ centigrade to $150°$ centigrade.

A further desirable embodiment of the present invention is a method of controlling soil pests by disposing a pest controlling quantity of the hereinbefore described composition in soil in which pests are to be controlled.

A wide variety of soil fumigants may be employed including 1,3-dichloropropene compositions and 1,2-dibromoethane compositions. Compositions of commercial purity are satisfactory for the practice of the present invention. Typically, a commercial 1,3-dichloropropene composition may contain 15.5 percent 1,2-dichloropropane, 42 percent cis and 36.5 trans 1,3-dichloropropene.

Biologically active organic materials, such as organic pesticide swellable pesticide insoluble polymers useful in the practice of the present invention are any polymers which are water insoluble and which swell on contact with a liquid soil pesticide. Useful polymers may swell on contact with water. However, additional swelling must occur when contacted with the pesticide. Selection of a polymer for use with any pesticide is readily accomplished by determining a swelling index for the polymer particles in the particular pesticide to be imbibed.

Generally, such swelling index is readily determined by immersing a particular polymer to be evaluated in the desired pesticide or liquid pesticide composition and determining the volume per unit weight of polymer after a period of about 30 minutes. The ratio of the volume per unit weight with organic liquid provides the swelling index. If the polymer is soluble, the swelling index is infinite. If the swelling index is greater than about 1.2, the polymer particles are useful in the practice of the present invention. Beneficially for most applications, a swelling index of at least 1.5 and preferably greater than about 3 is desirable. It is critical to the practice of the present invention to employ a crosslinked polymer which swells but does not dissolve. If the polymer swells in the presence of the organic liquid, it is suitable for the practice of the present invention. However, for most applications it is desirable to employ a polymer which is crosslinked to a sufficient degree that it exhibits a swelling index between about 1.5 and 50 and preferably between about 3 and 50. A wide variety of polymeric materials are employed with benefit. Such polymers include polymers of styrenes and substituted styrenes; polyvinyl chloride copolymers of vinyl chloride such as a copolymer of 60 weight percent vinyl chloride and 40 weight percent vinyl acetate; polymers and copolymers of vinylidene chloride including a copolymer of 75 percent vinylidene chloride and 25 percent acrylonitrile; acrylic polymers such as polymers of methyl methacrylate, ethyl acrylate and the like. In general, the chemical composition of the polymers is not critical. The polymers must show significant swelling; that is, at least a 25 percent increase in volume in a period of at least 30 minutes in the organic liquid to which the polymers are required to respond under desired service conditions of temperature and pressure. Particularly advantageous materials which respond to a wide variety of organic liquids are polymers of styrene such as polystyrene, and polymers of styrene and divinylbenzene containing up to about 10 weight percent divinylbenzene. For general use with aliphatic and aromatic hydrocarbons, alkylstyrene polymers and copolymers are of particular benefit. Such alkylstyrene polymers swell very rapidly on contact with hydrocarbons. Generally, the more rapid the swelling of the polymer, the more rapid the shutoff when the organic liquid is contacted. Alkylstyrene polymers and copolymers usually show substantial swelling when in contact with the liquid biologically active organic compound in less than 1 minute.

Preferably, crosslinked polymers and copolymers of styrenes, and advantageously of tertiary-alkylstyrenes, are utilized as the imbibing agent in the process of this invention. Those alkylstyrenes which can be used to prepare these polymers have alkyl groups containing from four to twenty, and preferably from four to twelve, carbon atoms, such as: tertiary-alkylstyrenes including, for example, p-tert-octylstyrene, and p-tert-eicosylstyrene; n-alkylstyrenes including, for example, n-butylstyrene, n-amylstyrene, n-hexylstyrene, n-octylstyrene, n-dodecylstyrene, n-octadecylstyrene, and n-eicosylstyrene; sec-alkylstyrenes including, for example, sec-butylstyrene, sec-hexylstyrene, sec-octylstyrene, sec-dodecylstyrene, sec-octadecylstyrene, and sec-eicosylstyrene; isoalkyl-styrenes including, for example, isobutylstyrene, iso-amylstyrene, iso-hexylstyrene, isooctylstyrene, isododecylstyrene, isooctadecylstyrene and isoeicosylstyrene; and copolymers thereof.

Especially preferred for use in the practice of the invention are crosslinked copolymers of such alkylstyrenes as heretofore described and an alkyl ester derived from $C_1$ to $C_{24}$ alcohol and acrylic or methacrylic acid or mixtures thereof.

Suitable monomers which may be employed as comonomers with the alkylstyrene include such materials as vinylnaphthalenes, styrene, vinyltoluenes, alphamethylstyrene, ring substituted alpha-methylstyrenes, halostyrenes, arylstyrenes and alkarylstyrenes; methacrylic esters, acrylic esters, fumarate esters and half esters, maleate esters and half esters, itaconate esters and half esters, vinyl biphenyls, vinyl esters of aliphatic carboxylic acids, alkyl vinyl ethers, alkyl vinyl ketones, alpha-olefins, isoolefins, butadiene, isoprene, dimethylbutadiene, acrylonitrile, methacrylonitrile and the like.

It is desirable that the polymers used in the process of the invention contain a slight amount of crosslinking agent, preferably in the range of from about 0.01 to 2 percent by weight. The most efficient imbibition of volatile organic liquid compositions occurs when the level of crosslinking agent is less than about 1 percent since this permits the polymers to swell easily and imbibe a substantial volume of the compositions.

Crosslinking agents which can be used in preparing the imbibing polymers suitable for use in the present invention include polyethylenically unsaturated compounds such as divinylbenzene, diethylene glycol dimethacrylate, diisopropenylbenzene, diisopropenyldiphenyl, diallylmaleate, diallylphthalate, allylacrylates, allylmethacrylates, allylfumarates, allylitaconates, alkyd resin types, butadiene or isoprene polymers, cyclooctadiene, methylene-norbornylenes, divinyl phthalates, vinylisopropenylbenzene, divinylbiphenyl, as well as any other di-or poly-functional compounds known to be of use as a cross-linking agent in these polymeric vinyl addition compositions. Normally, the polymer containing the cross-linking agent swells with the imbibed soil fumigants. If there is too much crosslinking agent, the imbibition takes an unreasonably long time or the polymer is unable to imbibe a sufficient quantity of the compositions. If the imbibitional polymer contains no crosslinking agent or too little crosslinking agent, then it will dissolve eventually in the pesticide or other biologically active organic material resulting, for example, in a non-discrete, non-particulate mass of polymer thickened liquid.

Polymers for the practice of the method of the present invention may be prepared by any convenient technique, either suspension, emulsion or mass polymerization free radical or ionically catalyzed. Generally, the method of preparation is selected to provide polymer in the most convenient form for any particular application. Thus, if it is desired to have free flowing, readily packed beads, generally suspension polymerization is employed to provide a plurality of small beads. If it is desired to obtain a bead having the maximum amount of polymer surface and a relatively high permeability rate toward volatile liquid pesticides, it is oftentimes desirable to employ an emulsion polymerization technique and recover the polymer by spray drying. If it is desired to obtain a body of predetermined configuration, it is oftentimes beneficial to employ a mass polymerization technique wherein a polymer-insoluble diluent is employed. Techniques for the preparation of such porous polymers are disclosed in U.S. Pat. No. 3,322,695, the teachings of which are herewith incorporated by reference. Such porous polymers can also be prepared by either suspension or mass polymerization. Alternately, satisfactory pesticidal or biologically active compositions are prepared by mass or suspension polymerization with subsequent comminution of the polymer prepared by the mass technique. The particle size of such polymers is selected in accordance with the desired application and release rate, generally unswollen particles having diameters of from about 100 microns to about 3,000 microns. Preferably, the diameters range from about 200 microns to 1,500 microns. If rapid release of the composition is desired, smaller diameter particles are employed, whereas if slower release rate is desired, larger diameter particles are employed. In a most desired employment of the invention, it is generally more preferable to incorporate in the composition as much pesticide as possible and as little of the pesticide insoluble crosslinked polymer.

The pesticide or other biologically active organic composition can be incorpoated in the swellable polymer in a variety of techniques. If the pesticide is liquid at room temperature, it may be admixed with an appropriate amount of the imbibing polymer and the mixture allowed to stand until the particles have imbibed the pesticide. The time for imbibition of the pesticide can be reduced by elevating the temperature of the mixture under sub, super, or atmospheric pressure depending on the vapor pressure characteristics of the pesticide composition to be imbibed. In the event that a solvent for the pesticide is employed, the rate of release of the pesticide can be varied by changing the volatility of the solvent as well as the concentration of solvent-pesticide mixture. If the pesticide is a solid at ambient temperature, a solvent may be employed to dissolve the pesticide and permit imbibition. The imbibing polymer may be mixed with the pesticide at or above the composition melting point to provide an imbibed composition. In the event that the organic composition can be mixed with the appropriate monomers prior to the polymerization thereof the resultant mass of swollen particles generally is treated with from about 3 to 20 parts by weight of a flow control additive. Generally, the compositions in accordance with the present invention employ from about 2 to 20 parts by weight of the swellable insoluble polymer from about 95 to 60 parts by weight of the organic biologically active composition and from about 3 to 20 parts by weight of a flow control additive. Swollen beads, for example, containing 90 parts by weight of biologically active and 10 parts by weight of polymer are in the form of a stiff gel with some tendency for clumping and exhibit a reluctance to flow. By the addition of a liquid flow control agent, for example 3 to 20 parts by weight of ethylene glycol, diethylene glycol and, particularly desirable, triethylene glycol, and tetraethylene glycol, and the equivalent propylene glycols as well as glycerol, the bead mass will assume the appearance of a grainy liquid which can be readily pumped and handled in conventional liquid dispensing apparatus. The grainy appearance of the liquid is somewhat deceptive in that one would assume that such obvious gel particles would block small orifices. However, the gel particles appear to be sufficiently flexible that they readily pass through openings smaller than their diameter under the influence of moderate pressure.

The flow, adhesion, and release properties of a swollen bead mass may readily be controlled by the use of various additives. The flow control additive such as those hereinbefore set forth may be added before, after or during the swelling of the beads or particles.

If it is desired to employ the pesticide as a dry granular material, the swollen particles are readily admixed with from about 3 to 20 parts by weight of a solid particulate flow control agent such as vermiculite, oat hulls, ground corn cobs, sand, clay and the like. Particularly advantageous is a mixture of vermiculite and fine ground calcium silicate in a proportion of about 10 to 1 to 50 to 1.

EXAMPLE 1

In order to illustrate the present invention, a laboratory experiment was conducted to demonstrate the relative reduction in volatility of the material in accordance with the invention compared to conventional practice. A standard crown cap (clamp on beverage bottle cap) was modified by removing the cork liner and the remaining lacquer was removed by washing with methylethyl ketone. The sample to be tested was then added to the crown cap evaporating dish by means of a hypodermic syringe and needle. The material to be tested was then covered with 4 grams of sand of a variety referred to as Manistee/Bunker Hill. The sand was leveled and the crown cap evaporating dish was immediately weighed on a balance having electronic digital read out of the weight of the evaporating dish and contents and recorded periodically for a period of about 2 hours. Three samples were employed:

Sample A consisted of 90 parts by weight of 1,3-dichloropropene (Commercial grade was used), imbibed in 5 parts by weight of a polymer which was about 99.5 weight percent polystyrene and about 0.5 weight percent divinylbenzene which was treated with 5 parts by weight of ethylene glycol. Sample B employed commercial 1,3-dichloropropene and sand only. Sample C used 78.3 parts by weight of 1,3-dichloropropene, 8.7 parts by weight of the polymer employed in Sample A and 13 parts by weight of triethylene glycol. The results are set forth in the follwing table. Under the heading "Time", the time in minutes represents the time the sample was on the balance. "Weight" indicates the gross weight of the sample. Columns headed "1,3-dichloropropene" are the calculated weight of the 1,3-dichloropropene remaining in the sample, all weights being in grams. The experiments were conducted indoors at the ambient temperature. For ease of illustration, the results are plotted in the accompanying FIGURE. The swollen polymer particles were about 0.5 millimeter in diameter.

TABLE

| A | | | | B | | | C | | | |
|---|---|---|---|---|---|---|---|---|---|---|
| Time | Weight | Mix[1] | Tel[2] | Time | Weight | Tel[2] | Time | Weight | Mix[1] | Tel[2] |
| 0 | 8.13 | 1.72 | 1.55 | 0 | 7.95 | 1.55 | 0 | 8.23 | 1.77 | 1.39 |
| 1 | 8.10 | 1.69 | 1.52 | 1 | 7.91 | 1.51 | 1 | 8.20 | 1.74 | 1.36 |
| 2 | 8.10 | 1.69 | 1.52 | 2 | 7.86 | 1.46 | 2 | | | |
| 5 | 8.06 | 1.65 | 1.49 | 5 | 7.82 | 1.42 | 5 | 8.14 | 1.68 | 1.32 |
| 10 | 8.01 | 1.60 | 1.44 | 10 | | | 10 | | | |
| 15 | | | | 15 | 7.70 | 1.30 | 15 | | | |
| 20 | 7.94 | 1.53 | 1.38 | 20 | | | 20 | 8.04 | 1.58 | 1.24 |
| 25 | | | | 25 | 7.52 | 1.12 | 25 | | | |
| 45 | | | | 45 | | | 45 | 7.92 | 1.46 | 1.14 |
| 50 | | | | 50 | 7.23 | 0.83 | 50 | | | |
| 60 | 7.67 | 1.26 | 1.13 | 60 | | | 60 | | | |
| 65 | 7.55 | 1.14 | 1.03 | 65 | | | 65 | | | |
| 70 | | | | 70 | | | 70 | 7.79 | 1.33 | 1.04 |
| 80 | | | | 80 | 6.90 | 0.50 | 80 | | | |
| 105 | | | | 105 | | | 105 | 7.67 | 1.21 | 0.95 |
| 115 | | | | 115 | 6.53 | 0.13 | 115 | | | |
| 120 | 7.43 | 1.02 | 0.92 | 120 | | | 120 | | | |

TABLE-continued

| | A | | | | B | | | C | | |
|---|---|---|---|---|---|---|---|---|---|---|
| Time | Weight | Mix[1] | Tel[2] | Time | Weight | Tel[2] | Time | Weight | Mix[1] | Tel[2] |
| 187 | | | | 187 | | | 187 | 7.52 | 1.06 | 0.83 |
| 195 | 7.26 | 0.85 | 0.77 | 195 | | | 195 | | | |

[1]Weight mixture of 1,3-dichloropropene + additive.
[2]Calculated weight of 1,3-dichloropropene.

When fumigant swollen particles in accordance with the present invention are disposed within the ground at a depth of ten inches to provide five gallons per acre of commercial 1,3-dichloropropene, satisfactory control of ground living pests is obtained for a growing season with soybeans and corn. Particles in accordance with the present invention are satisfactory for ground living pest control with other crops.

EXAMPLE 2

A solution of 0,0-diethyl-0-3,5,6-trichloro-2-pyridyl phosphorothioate (hereinafter referred to as Compound I) weighing 50 grams, the solution is 52 percent by weight of the Compound I in methylene chloride. To this solution, 1 gram of paraffin wax is added and dissolved therein. Subsequently, 1.5 grams of lightly cross-linked polystyrene containing 99.9 weight percent styrene and 0.1 weight percent divinylbenzene is added thereto. The polymer particles are in the form of beads having a diameter of about 300 microns. The mixture is permitted to stand at room temperature until no further swelling of the polymer particles is observed and some liquid remained. Less than 0.5 gram of additional polymer particles are added to imbibe the remaining observable liquid. Vermiculite having approximate density of 8 pounds per cubic foot is added and tumbled with the smaller beads. The beads form a coating on the vermiculite. The coated vermiculite is then subjected to an air stream at ambient temperature to remove the methylene chloride for recovery. The remaining material is vermiculite coated with the phosphorothioate swollen polymer particles. The rate of release of the phosphorothioate is reduced by a factor in excess of 2 relative to the rate of release of the Compound I alone.

EXAMPLE 3

The procedure of Example 2 is repeated with the exceptions that the paraffin wax was replaced with dibutylphthalate at a 5 weight percent level based on Compound I, and the resultant swollen particles are admixed with a fine particle dense clay which replaced the vermiculite resulting in a relatively dense particulate material which readily penetrates thatch on grass. The particles of Examples 2 and 3 are readily tilled into soil for extended release of the phosphorothioate.

EXAMPLE 4

2-(chloro-6-(trichloromethyl)pyridine (Compound II) is employed as a 1 to 1 by weight solution in methylene chloride which is prepared by gentle warming and agitation. To 50 grams of the resultant mixture is added 1.5 grams of the styrene-divinylbenzene polymer of Example 2. The resultant mixture is stirred until no additional imbibition of the solution is observed. Less than 0.5 gram of additional polymer particles is added to remove free liquid present. The resultant particles are then agitated with a synthetic calcium silicate commercially available under the trade designation of Microcel C sold by Johns-Manville Corporation. Particle size of such calcium silicate is below 0.1 micron, has a density between 4 and 14 pounds per cubic foot and a surface area of from about 94 to 200 square meters per gram. Methylene chloride is removed by means of exposing swollen particles to an air stream. On removal of the methylene chloride, a dry flowable mixture is obtained which may be employed as nitrogen stabilizer and a toxin for nitrosomonas without the requirement that the material immediately be covered with soil.

EXAMPLE 5

Compound II is melted and admixed with 1 gram of polymer of Example 2 for each 15 grams of Compound II with stirring. One gram of paraffin wax per 15 grams of Compound II is also added. Molten urea is prepared and the foregoing mixture added thereto with vigorous stirring. The resultant mixture is cooled below the melting point of the urea which now contains Compound II controlled release material encapsulated within the urea; and when prilled or ground to particulate form provides a relatively stable combination fertilizer-nitrogen stabilizer and toxin for nitrosomonas.

EXAMPLE 6

Employing the imbibed biologically active pyridine of Example 4, prilled urea is readily coated by admixing the swollen plastic particles with prilled urea and removing the methylene chloride in an air stream to provide urea prills coated with the biologically active release controlled particles.

EXAMPLE 7

A 20 weight percent solution of 0,0-diethyl-0-(2-isopropyl-6-methyl-4-pyrimidinyl)phosphorothioate, Compound III, in xylene is heated under vacuum to remove about 98 percent of the xylene. Ten parts by weight of Compound III are dissolved in methylene chloride containing 2 weight percent paraffin wax based on the weight of Compound III. The unswollen plastic particles as used in Example 2 are added to 50 grams of the methylene chloride solution of Compound III. One and one-half grams of unswollen plastic particles as employed in Example 2 are employed and subsequently less than 0.5 gram added to imbibe remaining free liquid. A fine screened Montmorrillonite clay is added to the swollen plastic particles while the methylene chloride contained therein is removed by an air stream for recovery. The residue is a mass of swollen polymer particles containing the biologically active Compound III subsequentially coated with clay to provide controlled release biologically active material.

EXAMPLE 8

The procedure of Example 7 is repeated with the exception that the paraffin wax was replaced with 2 grams of dibutylphthalate resulting in swollen plastic particles having increased adhesion to the clay particles.

EXAMPLE 9

The procedure of Example 7 is repeated with the exception that Compound III is employed as a 50 weight percent solution in xylene to prepare delayed release particles. In the event increased adhesion to plant leaf or other surface is desired, a soluble rubbery material such as poly-2-ethylhexylacrylate is employed with polypropylene glycol as a lubricant.

EXAMPLE 10

The polymer particles containing Compound I as prepared in Example 3 without the clay coating are modified by adding a trace quantity of Du Pont oil Red A to permit visual identification of the particles. The colored particles are wetted wtih propylene glycol and mixed into a commercially available latex paint, the latex paint is white interior flat latex paint sold by the Sherwin-Williams Company. The so-treated paint is applied to polystyrene foam, wood and a plastic substrate. The foregoing procedure is repeated using an unpigmented 60 to 40 by weight butadiene styrene copolymer latex. In each of the cases, the red swollen particles containing Compound I are uniformly distributed in the paint films, thus permitting the application of biologically active materials to protect a wide variety of materials from various pest organisms.

EXAMPLE 11

A solution of 20 grams of orthophenylphenol is dissolved in 50 grams of methylene chloride. The resultant solution is imbibed into 2.5 grams of the swellable plastic particles as used in Example 1. The resultant swollen particles are maintained in an air stream to remove methylene chloride therefrom. When the methylene chloride is removed, a vermiculite is added to the orthophenylphenol swollen plastic mass with agitation. The final material is a free-flowing powder containing orthophenylphenol in a controlled release form.

Similar beneficial results are obtained when 0,0-diethyl-0-(3,5,6-trichloro-2-pyridol)phosphorothioate, 0,0-diethyl-0-(2-isopropyl-6-methyl-4-pyrimidyl)phosphorothioate and other biologically active compounds are employed in the manner hereinbefore set forth.

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appended claims.

What is claimed is:

1. A fumigant composition, the fumigant composition comprising a plurality of fumigant swellable fumigant insoluble crosslinked polymer particles, the polymer particles having a swelling index of from about 1.5 to 50, the polymer particles having imbibed therein from about 3 to 50 times the unswollen volume of the particles of a volatile soil fumigant which boils at atmospheric pressure at a temperature of from about −100° centigrade to 350° C.

2. The fumigant composition of claim 1 wherein the fumigant comprises 1,3-dichloropropene.

3. The fumigant composition of claim 1 wherein the polymer particles are crosslinked polystyrene.

4. The composition of claim 3 wherein the swelling index is from about 3 to about 50.

5. The fumigant composition of claim 1 wherein the volatile fumigant comprises 1,3-dichloropropene and the polymer particles are crosslinked polystyrene.

6. The composition of claim 1 including from about 3 to 20 parts by weight per 100 parts by weight of the fumigant composition of a flow control additive.

7. The composition of claim 6 wherein the flow control additive is particulate.

8. The composition of claim 6 wherein the flow control additive is a liquid.

9. A method of controlling soil pests by disposing a pest controlling quantity of a fumigant composition, the fumigant composition comprising a plurality of fumigant swellable fumigant insoluble crosslinked polymer particles, the polymer particles having a swelling index of from about 1.5 to 50, the polymer particles having imbibed therein from about 3 to 50 times the unswollen volume of the particles of a volatile soil fumigant which boils at atmospheric pressure at a temperature of from about −100° centigrade to 350° C.

10. The method of claim 9 wherein the fumigant comprises 1,3-dichloropropene.

11. The method of claim 9 wherein the polymer particles are crosslinked polystyrene.

12. The method of claim 11 wherein the swelling index is from about 3 to about 50.

13. The method of claim 9 wherein the volatile fumigant comprises 1,3-dichloropropene and the polymer particles are crosslinked polystyrene.

14. The method of claim 9 including from about 3 to 20 parts by weight per 100 parts by weight of the fumigant composition of a flow control additive.

15. The method of claim 14 wherein the flow control additive is particulate.

16. The method of claim 14 wherein the flow control additive is a liquid.

17. A composition containing biologically active organic materials, the composition comprising a plurality of organic chemically swellable organic chemically insoluble crosslinked polymer particles, the polymer particles having a swelling index of from about 1.2 to 50; the particles having imbibed therein from about 1.2 to 50 times the unswollen volume of the particles of a volatile biologically active organic chemical composition which boils at atmospheric pressure at a temperature of from about −100° centigrade to about 350° centigrade and is capable of diffusing out of said particles.

18. A method of dispensing a biologically active organic chemical composition by disposing said biologically active composition comprising a plurality of organic chemically swellable organic chemically insoluble crosslinked polymer particles, the polymer particles having a swelling index of from about 1.2 to 50; the polymer particles having imbibed therein from about 3 to 50 times the unswollen volume of the particles of a volatile biologically active organic chemical composition which boils at atmospheric pressure at a temperature of from about −100° centigrade to about 350° centigrade and can diffuse from said particles.

* * * * *